(12) United States Patent
Moorman et al.

(10) Patent No.: US 8,588,908 B2
(45) Date of Patent: Nov. 19, 2013

(54) SYSTEM, METHOD AND COMPUTER PROGRAM PRODUCT FOR DETECTION OF CHANGES IN HEALTH STATUS AND RISK OF IMMINENT ILLNESS

(75) Inventors: J. Randall Moorman, Charlottesville, VA (US); Douglas E. Lake, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 132 days.

(21) Appl. No.: 12/866,056

(22) PCT Filed: Feb. 4, 2009

(86) PCT No.: PCT/US2009/033082
§ 371 (c)(1),
(2), (4) Date: Aug. 4, 2010

(87) PCT Pub. No.: WO2009/100133
PCT Pub. Date: Aug. 13, 2009

(65) Prior Publication Data
US 2010/0324436 A1 Dec. 23, 2010

Related U.S. Application Data

(60) Provisional application No. 61/025,989, filed on Feb. 4, 2008, provisional application No. 61/043,598, filed on Apr. 9, 2008.

(51) Int. Cl.
*A61N 1/365* (2006.01)
(52) U.S. Cl.
USPC ............................................ 607/14; 600/518

(58) Field of Classification Search
USPC .............. 607/5, 14, 18, 25–26; 600/508–509, 600/518
See application file for complete search history.

(56) References Cited

U.S. PATENT DOCUMENTS

| | | | |
|---|---|---|---|
| 5,328,442 A | 7/1994 | Levine | |
| 5,544,651 A | 8/1996 | Wilk | |
| 6,104,949 A | 8/2000 | Pitts Crick | |
| 6,192,273 B1 * | 2/2001 | Igel et al. | 607/14 |
| 6,216,032 B1 | 4/2001 | Griffin | |
| 6,328,699 B1 | 12/2001 | Eigler | |
| 6,330,469 B1 | 12/2001 | Griffin | |
| 6,336,903 B1 | 1/2002 | Bardy | |
| 6,454,707 B1 | 9/2002 | Casscells | |
| 6,473,640 B1 | 10/2002 | Erlebacher | |

(Continued)

OTHER PUBLICATIONS

Adamson, "Reducing Events in Patients with Chronic Heart Failure (REDUCEhf) Study Design: Continuous Hemodynamic Monitoring with an Implantable Defibrillator", Clinical Cardiology 2007, pp. 567-575, vol. 30, Iss. 11, Wiley Periodicols Inc.

(Continued)

*Primary Examiner* — Rex R Holmes
(74) *Attorney, Agent, or Firm* — Robert J. Decker

(57) ABSTRACT

A method for analysis of cardiac rhythm and RR interval time series based on entropy related data and entropy based measures. The information is related to but distinct from entropy, and is derived from histograms of interval match counts in which the y-axis is the frequency of intervals of length in that have the match count given on the x-axis. The phenotype of the histogram informs on the presence of atrial fibrillation or, in the presence of sinus rhythm, the degree of congestive heart failure.

17 Claims, 7 Drawing Sheets

(56) References Cited

U.S. PATENT DOCUMENTS

| | | |
|---|---|---|
| 6,514,226 B1 | 2/2003 | Levin |
| 6,567,699 B2 | 5/2003 | Alferness |
| 6,643,548 B1 | 11/2003 | Mai |
| 6,645,153 B2 | 11/2003 | Kroll |
| 6,766,194 B1 | 7/2004 | Kroll |
| 6,804,551 B2 | 10/2004 | Griffin |
| 6,811,537 B2 | 11/2004 | Bardy |
| 6,829,503 B2 | 12/2004 | Alt |
| 6,856,831 B2 | 2/2005 | Griffin |
| 6,908,437 B2 | 6/2005 | Bardy |
| 6,961,613 B2 | 11/2005 | Bjorling |
| 7,020,521 B1 | 3/2006 | Brewer |
| 7,043,301 B1 | 5/2006 | Kroll |
| 7,070,568 B1 | 7/2006 | Koh |
| 7,072,715 B1 | 7/2006 | Bradley |
| 7,117,028 B2 | 10/2006 | Bardy |
| 7,127,290 B2 | 10/2006 | Girouard |
| 7,184,816 B2 | 2/2007 | Bjorling |
| 7,315,760 B2 | 1/2008 | Brodnick |
| 2002/0099302 A1 | 7/2002 | Bardy |
| 2002/0123674 A1 | 9/2002 | Plicchi |
| 2002/0169484 A1 | 11/2002 | Mathis |
| 2003/0055461 A1 | 3/2003 | Girouard |
| 2003/0149367 A1 | 8/2003 | Kroll |
| 2003/0149453 A1 | 8/2003 | Kroll |
| 2004/0106958 A1 | 6/2004 | Mathis |
| 2004/0116819 A1 | 6/2004 | Alt |
| 2004/0116971 A1 | 6/2004 | Bjorling |
| 2004/0127951 A1 | 7/2004 | Jarverud |
| 2004/0147982 A1 | 7/2004 | Bardy |
| 2004/0230127 A1 | 11/2004 | Bardy |
| 2005/0004607 A1 | 1/2005 | Bjorling |
| 2005/0085863 A1 | 4/2005 | Brodnick |
| 2005/0096510 A1 | 5/2005 | Bardy |
| 2005/0137480 A1 | 6/2005 | Alt |
| 2005/0137484 A1 | 6/2005 | Griffin |
| 2005/0143787 A1 | 6/2005 | Boveja |
| 2005/0215914 A1 | 9/2005 | Bornzin |
| 2005/0234352 A1 | 10/2005 | Bardy |
| 2005/0288726 A1 | 12/2005 | Gollasch |
| 2006/0074329 A1 | 4/2006 | Ferguson |
| 2006/0116581 A1 | 6/2006 | Zdeblick |
| 2006/0161070 A1 | 7/2006 | Siejko |
| 2006/0161211 A1 | 7/2006 | Thompson |
| 2006/0224190 A1 | 10/2006 | Gill |
| 2006/0235325 A1 | 10/2006 | Holmstrom |
| 2007/0043299 A1 | 2/2007 | Wariar |
| 2007/0073168 A1 | 3/2007 | Zhang |
| 2007/0112278 A1 | 5/2007 | Viertio-Oja |
| 2007/0179399 A1* | 8/2007 | Viertio-Oja et al. .......... 600/559 |
| 2007/0299349 A1 | 12/2007 | Alt |

OTHER PUBLICATIONS

Adamson, "Continuous Autonomic Assessment in Patients with Symptomatic Heart Failure: Prognostic Value of Heart Rate Variability Measured by an Implanted Cardiac Resynchronization Device", Circulation, 2004, pp. 2389-2394, vol. 110, American Heart Association.

Costa, "Multiscale Entropy Analysis of Complex Physiologic Time Series", Physical Review Letters, 2002, pp. 068102-1-068102-4, vol. 89, No. 6, The American Physical Society.

Costa, "Multiscale Entropy Analysis of Biological Signals", Physical Review E, 2005, pp. 021906-01-021906-18, vol. 71, Iss. 2, The American Physical Society.

Lake, "Renyi Entropy Measures of Heart Rate Gaussianity", IEEE Transactions on Biomedical Engineering, 2006, pp. 21-27, vol. 53, No. 1.

Lake, "Sample Entropy Analysis of Neonatal Heart Rate Variability", American Journal of Physiology Regulatory, Integrative and Comparative Physiology, 2002, R789-R797, vol. 283, American Physiological Society.

Moorman, "Heart Rate Characteristics Monitoring in Neonatal Sepsis", IEEE Transactions on Biomedical Engineering, 2006, pp. 126-132, vol. 53, No. 1.

Pincus, "A Regularity Statistic for Medical Data Analysis", Journal of Clinical Monitoring 1991, pp. 335-345, vol. 7, No. 4, Little, Brown and Company.

Raj, "Activity-Responsive Acing Produces Long-Term Heart Rate Variability", Journal of Cardiovascular Electrophysiology, 2004, pp. 179-183, vol. 15, No. 2.

Raj, Letter regarding article by Adamson et al, "Continuous Autonomic Assessment in Patients with Symptomatic Heart Failure: Prognostic Value of Heart Rate Variability Measured by an Implanted Cardiac Resynchronization Device", Circulation, 2005, pp. e37-e38, vol. 112, No. 2, American Heart Association.

Richman, "Sample Entropy Statistics and Testing for Order in Complex Physiological Signals", Communications in Statistics—Theory and Methods, 2006, pp. 1005-1019, vol. 36, Iss. 5, Taylor & Francis Group, LLC.

Richman, "Physiological Time Series Analysis using Approximate Entropy and Sample Entropy", American Journal of Physiology Hearth and Circulatory, 2000, pp. H2039-H2049, vol. 278, American Physiological Society.

* cited by examiner

SYSTEM, METHOD AND COMPUTER PROGRAM PRODUCT FOR DETECTION OF CHANGES IN HEALTH STATUS AND RISK OF IMMINENT ILLNESS

CROSS-REFERENCE TO RELATED APPLICATIONS

This application is a national stage filing of International Application No. PCT/US2009/033082, filed Feb. 4, 2009, which claims benefit under 35 U.S.C. §119(e) to U.S. Provisional Patent Application Ser. No. 61/025,989 filed on Feb. 4, 2008, and Ser. No. 61/043,598 filed on Apr. 9, 2008, the disclosures of which are hereby incorporated by reference in their entireties.

This application is also related to PCT application No. PCT/US2008/0600211, which is hereby incorporated by reference in Its entirety.

STATEMENT REGARDING FEDERALLY SPONSORED RESEARCH OR DEVELOPMENT

This invention was not made in the course of federally sponsored research or development.

THE NAMES OF THE PARTIES TO A JOINT RESEARCH AGREEMENT

This invention was not made in the course of joint research agreement.

BACKGROUND OF THE INVENTION

The present invention generally relates to the field of cardiology and in particular to detection and analysis of cardiac function. There is a serious need for detection of normal and abnormal cardiac rhythms as well as evaluation of the clinical status of the patient, e.g., detection of severe or worsening congestive heart failure, using heart rate (HR) or interbeat interval series.

A problem of enormous and growing concern in health care in America is hospitalization for worsening congestive heart failure (CHF). New medical therapies have prolonged the life of many with CHF, and implantable cardiac devices—implantable cardioverter-defibrillators (ICDs) and biventricular pacemakers—have been especially effective in prolonging life and reducing symptoms. ICDs are small battery-powered electrical impulse generators that are implanted in at-risk patients and are programmed to detect cardiac arrhythmia and correct it by delivering a jolt of electricity to the heart muscle. Most patients with single lead ICDs have reduced Left Ventricle (LV) function, and thus either have or are at risk for CHF syndromes. Other than heart rate and heart rate variability, and in some cases trans-thoracic impedance, no measures are currently available to gauge the degree of CHF over time. There is, however, potentially a great deal of clinical utility in doing so.

A new role for ICDs is as diagnostic monitors that might allow early detection of incipient volume overload. For example, modern pacemakers and defibrillators store several dimensions of physiological data representative of the functional status or physiological signals of the patient, including:
heart rate (HR)
heart rate variability (HRV)
amount of pacing in the atrium and the ventricle
patient activity, in hours per day
atrial fibrillation burden (only in devices with atrial leads)
arrhythmia log
respiration
trans-thoracic impedance, a measure of pulmonary vascular congestion
and any other relevant physiological signals The hope is that all of these parameters will yield clinically useful information about the status of the cardiovascular system and in particular the possibility of imminent decompensation. The presumption is that very early detection of volume overload can be treated at home with increased doses of medications, averting severe symptoms and the need for hospitalization.

These parameters, however, are currently presented to the physician for review without presenting any interpretation, and there are few studies of how these data can be of clinical use. It has been demonstrated that hospitalizations for heart disease is associated with a reduction in heart rate variability (HRV, a well-established measure of risk of cardiac events) measured by the standard deviation of 5-minute median A-A intervals (SDAAM) (the time between sensed, that is, non-paced, atrial depolarizations), reduction in patient activity, and increased heart rate (HR) at night. Although a patient with CHF may exhibit low HRV, there are usually a few beats that are distinct from the rest and will occur prematurely, followed by an extended pause so that the heart can catch-up to where it should have been absent the premature beat. These are termed premature ventricular beats or contractions (PVCs).

Although atrial fibrillation (AF) can be discerned using coefficient of sample entropy (COSEn), attempts at developing a diagnostic tool that distinguishes normal sinus rhythm (NSR) in patients with CHF from other patients with NSR using only very short heart rate time series have so far not succeeded. Such a method would be very useful in patients with ICDs, where the risk of CHF is high but the ability to do extended calculations is low. The long-felt need for a new method that addresses the limitations, disadvantages, and problems discussed above is evidenced by the many databases available for development and testing of new arrhythmia detection algorithms. Several of these databases, such as the MIT-BIH database, have been used during the development and testing of embodiments of the present disclosure.

Detection of AF can be accomplished with very high degrees of accuracy if an intra-atrial cardiac electrogram from an implanted pacing lead or a conventional EKG signal from skin electrodes is available. Neither is as non-obtrusive as a device that records the time from one arterial pulse waveform to the next, but such a non-invasive device can provide only the heart rate time series with no information about cardiac electrical activity. Thus, an algorithm and computer method for detecting arrhythmia or the clinical status of a patient using only a heart rate or pulse rate series is a desirable goal.

There is currently exists no single parameter to inform clinicians and patients of imminent problems such as CHF. Yet such an approach is sensible—combinations of data values may define specific profiles of clinical status. For example, a measure that combines an HRV measure, patient activity and nocturnal heart rate is very likely to be more useful than any of the measures alone. An aspect of an embodiment of the present invention comprises among other things, combining multiple data streams using optimized mathematical techniques.

BRIEF SUMMARY OF INVENTION

We have developed a new measure of heart rate entropy that changes in proportion to the degree of CHF. It is related to, but distinct from, sample entropy (SampEn) or the coefficient of sample entropy (COSEn) that we have previously developed. We find that we can distinguish CHF patients from normals using only an analysis of 12 beats every 30 minutes.

Aspects of various embodiments of the present disclosure comprise, but are not limited to, the following: systems and methods for analyses of physiological time series recorded by implanted cardiac devices, and for analyses of multiple simultaneously recorded series. While the embodiments are used herein for detection of incipient congestive heart failure episodes and atrial fibrillation using information from implanted pacemakers and cardioverter-defibrillators, other embodiments are contemplate to extend to other kinds of signals from internal and external measurement devices and monitors, and to other states of health and disease.

DETAILED DESCRIPTION OF THE INVENTION

Figure 1:
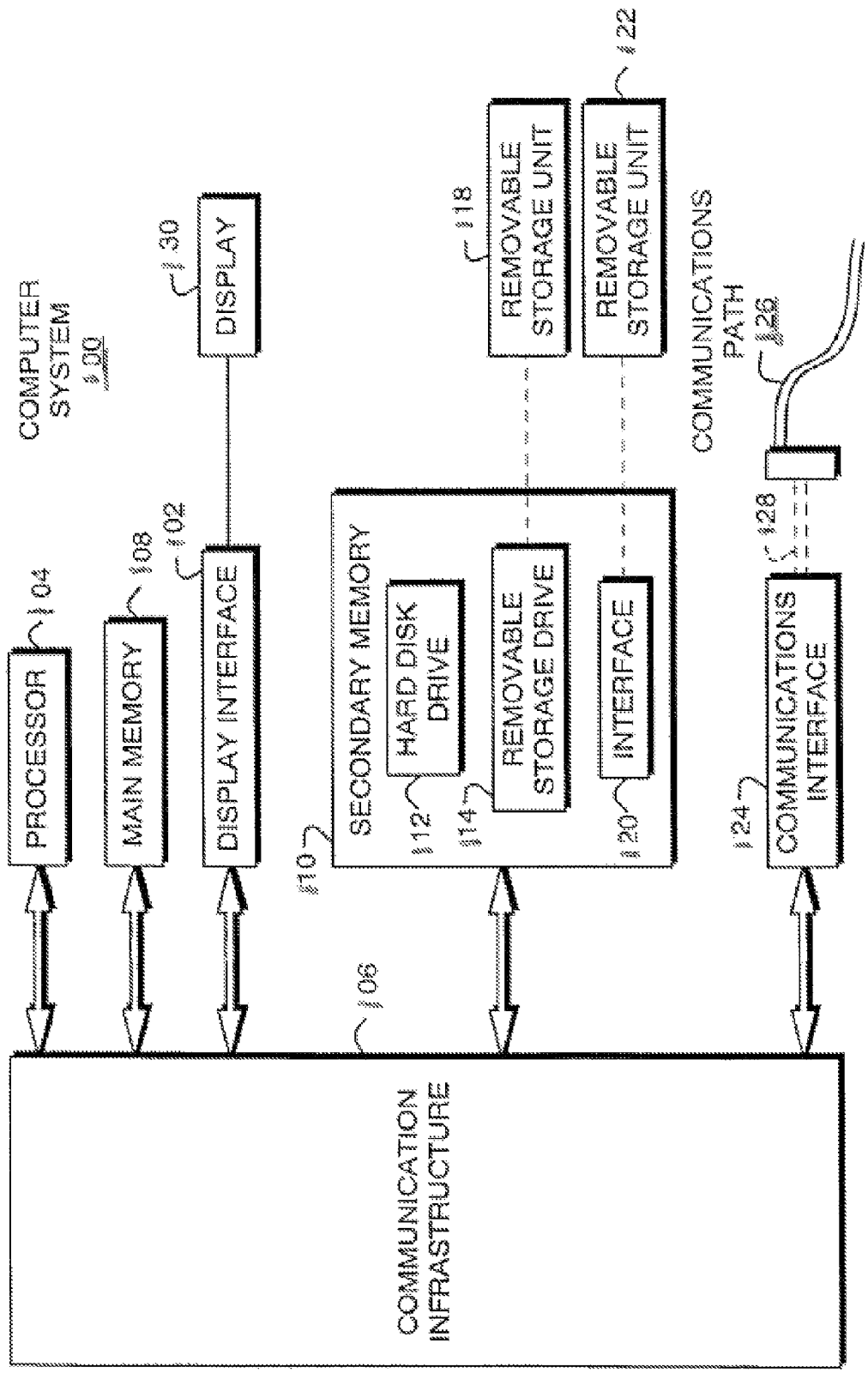
FIG. 1 is an illustrative diagram of a computer system.

Aspects of various embodiments of the present disclosure comprise, but are not limited to, the following: comparing time series representing periods of a cardiac rhythm with other series to generate numbers of matches to provide an entropy estimate. The numbers of matches may further be processed to generate a diagnostic output representative of a patient's abnormal cardiac rhythm and clinical status. No existing approaches employ optimized estimates of time series entropy or combine measurements across different kinds of time series data from implantable cardiac devices.

One embodiment of the present disclosure focuses on entropy estimation of time series time domain HRV data types. Generally speaking, this is a measure of the predictability or regularity of a time series. Entropy estimation of heart rate has been well-described for a number of years, and can distinguish normal long heart rate records from those of patients with CHF. For example, sample Entropy (SampEn) is a robust estimator of entropy in short biological and physiological time series. Multiscale entropy can be described based on sample entropy measure to accomplish this task. Entropy estimation of other measures listed above has not been described, but may hold important clinical information. For example, a current concept is that illness leads to reduced coupling among physiological systems, altering the entropy content of physiological signals.

An aspect of the present disclosure is to use optimized entropy calculations of time series information present in implantable devices to make early diagnosis of sub-acute, potentially catastrophic illness such as CHF. Each of the physiological signals listed above (e.g., HR, HRV, ect.) can be assessed in some way for its regularity or predictability using an entropy calculation. It has been found that illness leads to a reduction in complexity of physiological processes. Thus, time series of heart rate, heart rate variability parameters themselves (such as the standard deviation of short thoracic impedance, and intracardiac pressures) should show changes in entropy as clinical status changes. Of these, heart rate has been well-studied. An interesting finding is that patients with CHF have been reported to have increased entropy of heart rate time series, a finding that does not fit well with current knowledge. This apparent discrepancy has been resolved by showing that a multiscale entropy calculation demonstrated lower entropy in CHF patients, suggesting that too short a time scale fails to capture the predictability of normal heart rate control.

Embodiments discussed throughout the disclosure improve the detection of CHF. Various embodiments of the present disclosure may be based on several fundamental differences between the RR interval time series in CHF and in other clinical settings as well as important supplemental information provided by physiologic signals measuring activity, blood pressure, and respiration. Measurements of the RR interval series used to classify cardiac rhythms and clinical status fall into two basic categories of estimates of the moments and estimates of entropy rate to characterize heart rate dynamics. For analysis of multiple simultaneous signals, mathematical approaches to detect CHF can be placed into 3 categories: 1) moments; 2) entropy and entropy rate; and 3) cross-correlation and cross-entropy measures.

The first category includes measurements that are associated with established statistical methods, such as the mean, standard deviation, and coefficient of variation. The second category includes the family of Renyi entropy (or q-entropy) rates. The third category consists of measures of the association and interaction between the various physiologic signals. These include results from standard cross-spectral analysis including pair-wise correlations between signals at varying time-lags.

Embodiments of the present disclosure detect cardiac rhythms and clinical status of a patient based on a series of RR intervals or other physiological signals, which arise from a complex combination of both deterministic and stochastic physiological processes.

Sample entropy (SampEn) is a measure derived from chaos theory that reports on deterministic properties of time series. SampEn has better statistical properties than approximate entropy and has been utilized successfully on neonatal HR data to aid in the prediction of sepsis. SampEn has also been used as part of a promising new multiscale entropy (MSE) analysis technique to better discriminate adult HR data among normal, atrial fibrillation, and congestive heart failure patients.

For purposes of comparison, sample entropy is considered a deterministic approach to measuring complexity and order in heart rate variability. A complementary approach included in some embodiments is to consider HR and other physiological data sufficiently stochastic to model it as a random process. We have developed stochastic Renyi entropy rate measures that can be reliably estimated with a known family of statistical properties. An appropriate member of the family to emphasize is differential or quadratic entropy rates (q=2)

which is denoted by Q and calculated using the SampEn algorithm with optimized values for the parameters m and r.

These measures can be interpreted in ways that are analogous to the deterministic concepts of complexity and order. While developed under a stochastic framework, the algorithms are easily modified to compute deterministic approach measures that include both Approximate Entropy (ApEn) and SampEn. There are several basic differences between the stochastic approach and the deterministic approaches, and each has potential application to detection of congestive heart failure. The deterministic approach, for example, involves calculating probabilities while the stochastic approach calculates probability densities. The probabilities involve matching intervals of length m within a tolerance r and converting them to densities by dividing by the volume of the matching region, which is $(2r)^m$. This simply reduces to adding a factor of $\log(2r)$ to ApEn or SampEn. The stochastic approach becomes viable when the values converge as r tends to 0 and the deterministic approach is diverging.

With deterministic approaches, the values of m and r are fixed for all the analysis (sometimes signal length is also constant). This is done to enable comparison of a wider variety of processes, but has several disadvantages. The choices of m and r vary from study to study and comparison of results is not always possible. Optimal parameters can be chosen for other clinical settings. In one embodiment, we use both fixed value of r=50 msec as well as r=f(S.D.). With fixed values, there is always the possibility of encountering data that results in highly inaccurate entropy estimates, so included in this embodiment is the continued development of absolute entropy measures independent of m and r that are statistically reliable and allow for comparison between a wide range of HR data sets.

With the stochastic approach, the goal is to estimate a theoretical limiting value as r goes to zero. The value of r for estimation does not need to be fixed and can be optimized for each signal. In addition, for longer records we include in one embodiment the option of not fixing m and instead estimating the theoretical limiting value as m tends to infinity. One advantage of this general philosophy is that tolerances and interval lengths can be selected individually for each signal to ensure accurate estimates. Even if it is advantageous or necessary to compare signals at the same value of r, this embodiment flexibility allows using different tolerances for estimating and applying a correction factor.

This idea is particularly important in the current setting of estimating entropies of quantized RR intervals obtained from coarsely sampled EKG waveforms, as quantization of the signal can occur when the sampling rate is low. These scenarios mean that all tolerances r within the resolution will result in the exact same matches and the issue becomes what value r should be used to calculate the entropy rate. The proper choice is to pick the value midway between the quantized values of r. For example, the EKG signal was sampled at 250 Hz for some signals in the CHF database, and thus the RR intervals are at a resolution of 4 ms. In this case, all tolerances between, say, 12 and 16 milliseconds would be considered 14 for the $\log(2r)$ term. Different values are needed for signals from the NSR database and other signals in the CHF database that were sampled at 128 Hz and at a resolution of 7.8 msec. This continuity correction can be nontrivial when tolerances are close to the resolution of the data. Some embodiments optimize the accuracy and discriminating capability of the entropy measures. Undersampling can occur with other physiologic signals as well, and the embodiments robustly and accurately estimate entropy in spite of this problem.

As an example, we describe the use of entropy measures to discern abnormal cardiac rhythm and clinical status in RR interval time series from the canonical MIT-BIH CHF and NSR databases employing multivariable logistic regression and its variations. These databases are available at www.physionet.org and are described in Table 1. Most, if not all, of the rhythms are sinus with varying degrees of premature ventricular beats, or ventricular ectopy.

TABLE 1

MIT-BIH databases

| | Database | | |
|---|---|---|---|
| | NSR | CHF class 1-2 | CHF class 3-4 |
| Patients | 72 | 29 | 15 |
| Age | 20 to 76 | 34 to 79 | 22 to 63 |
| Male | 49% | not known | 73% |
| Duration (hours) | (72) (24) = 1728 | (29) (24) = 696 | (15) (24) = 360 |
| Sampling (Hz) | 128 | 128 | 250 |

NSR = normal sinus rhythm, CHF = congestive heart failure

We determined optimal values of m and r by calculating the error of the SampEn estimate for a wide range of both parameters. The results for distinguishing normal subjects with NSR from CHF patients with NSR using the MIT data bases are shown in the FIG. 2. Here, we analyzed non-overlapping 500 point segments of RR intervals.

Figure 2:
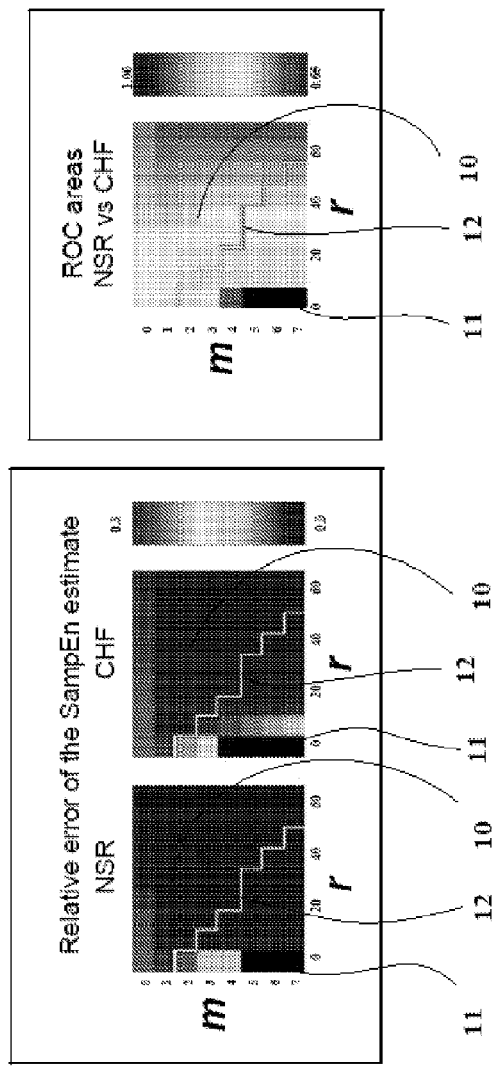
FIG. 2 depicts two charts showing the efficacy of parameters used in the SampEn algorithm.

In the maps of FIG. 2, the gray areas 10 represent favorable characteristics of the m, r pair—accurate entropy estimates in the left and middle panels, and good discrimination (measured as the receiver-operating characteristic, or ROC, area) in the right hand panel. Black areas 11 show m, r pairs where no matches were found and thus entropy could not be calculated. The area to the left of and below zigzag line 12 shows an m, r space where SampEn cannot be accurately determined in atrial fibrillation. This is a sensible result—that area of the plot requires long intervals that match closely, which is not the case for AF. These results demonstrate both the general method for optimal selection of m and r and specific findings for detecting CHF—m should be 1 or 2, and r should be about 20 msec. With these settings, SampEn alone provides distinction with ROC areas around 0.8.

In implanted devices, computing power and memory are currently limited, and analysis of 500 point segments is currently prohibitive. Therefore, a reduced sampling of parameters from a patient is beneficial. Thus, for the next analysis, we studied non-overlapping 16-point segments. Moment and entropy rate parameters described above were estimated for each record, and CHF detectors were developed using multivariable logistic regression analysis and an optimal subset of variables. With multiple physiologic signals, this approach would be expanded to include moment and entropy rate variables from each individual.

In this embodiment, an optimal subset of variables for detecting CHF were the quadratic or differential entropy rate (Q), the natural logarithm (ln) of the mean ($\mu$), and the log of the standard deviation ($\sigma$) of the RR intervals. This model has an ROC area of 0.750, which is highly significant as are each of the coefficients. The entropy rate is calculated using the SampEn algorithm with parameters m=1 and a tolerance r selected to ensure a number of matches in the numerator of at least the record length (in this case 16). This result aided in the development COSEn, which is described in more detail in PCT application No. PCT/US2008/060021. We also compare these results with the coefficient of variation $CV=\sigma/\mu$.

The results for other models are summarized below in Table 2. Subsets of parameters are evaluated using the significances of individual coefficients and of the overall model using the Wald statistic adjusted for repeated measures. The overall significance of the model can be converted to a Wald Z-statistic, which can be used to make a fair comparison among models with varying number of parameters. The results clearly demonstrate that the proposed approach that includes entropy measures as part of a multivariate model enhances the detection performance of CHF. Additional improvements are anticipated with the inclusion of entropy and cross-entropy measures from other available physiological signals.

TABLE 2

Model Performances on MIT NSR and CHF data bases

| Parameters | CHF ROC | Wald | Wald Z |
|---|---|---|---|
| $\log(\mu)$ | .708 | 21.4 | 14.5 |
| $\log(\sigma)$ | .659 | 9.2 | 5.8 |
| $\log(CV)$ | .638 | 5.1 | 2.9 |
| $\log(\mu), \log(\sigma)$ | .712 | 33.6 | 15.8 |
| Q | .741 | 17.8 | 11.9 |
| Q, $\ln(\mu), \log(\sigma)$ | .750 | 62.6 | 24.3 |

As discussed above, one way of quantifying one period of a cardiac rhythm is by its length (m). The length can be determined by, for example, sampling points on an EKG during one interval of the cardiac rhythm. A longer interval will have a greater number of samples than a shorter interval. An interval can be one period of the rhythm, for example an RR or AA interval, but it could also be any arbitrary size.

Once the intervals of a cardiac rhythm are quantified, they may be compared to determine whether the numbers of samples for each interval match. The intervals may be divided up into, for example, 12 interval series. Next, each interval may be compared with each other interval to determine the number of times that each interval matches another interval of the same series. Each interval therefore has a corresponding number of matches associated with it. For example, 7 intervals may have matched 0 times, 4 may match 1 time, and 1 may have matched 2 times. A resulting histogram of these values would appear similar to the left-most histogram of FIG. 3.

Figure 3:
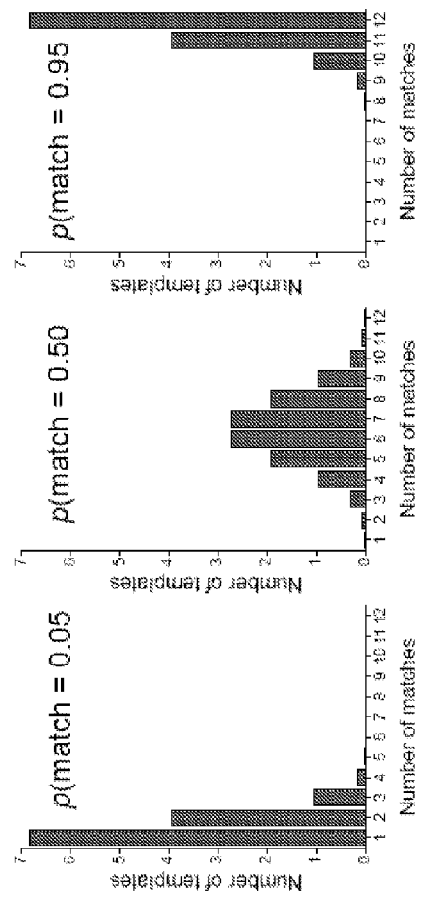
FIG. 3 depicts histograms of expected interval matches for different matching probabilities.

Histograms created in the method just described will have a predictable appearance depending on the entropy of the cardiac rhythm. To illustrate, as the tolerance r goes to zero, the distribution of interval match counts approximates the distribution of a random variable f(X) where X is a random RR interval of length m and f is the probability density function of X, e.g., left-most histogram of FIG. 3. For Gaussian random numbers, we expect −2 ln(interval match counts) to have a shifted chi-square distribution with m degrees of freedom, e.g., middle histogram of FIG. 3. If the RR intervals are independent, then the distribution of interval match counts (not including self-matches) is approximately binomial with n-m trials and success probability p equal to the probability of any interval matching within the tolerance r. FIG. 3 shows the expected results of interval match counts for 12-beat segments and p(match)=0.05, 0.50 and 0.95.

In the case of a rhythm with high entropy, as would be found in a patient with AF, it would be expected that there would be a low number of matches. This result corresponds to the left-most histogram of FIG. 3. As is well known in the art, a patient with CHF has low entropy, i.e., low HRV. Therefore, it would be expected that a high number of intervals would match. A resulting histogram would appear similar to the right-most histogram illustrated in FIG. 3.

Figure 4:
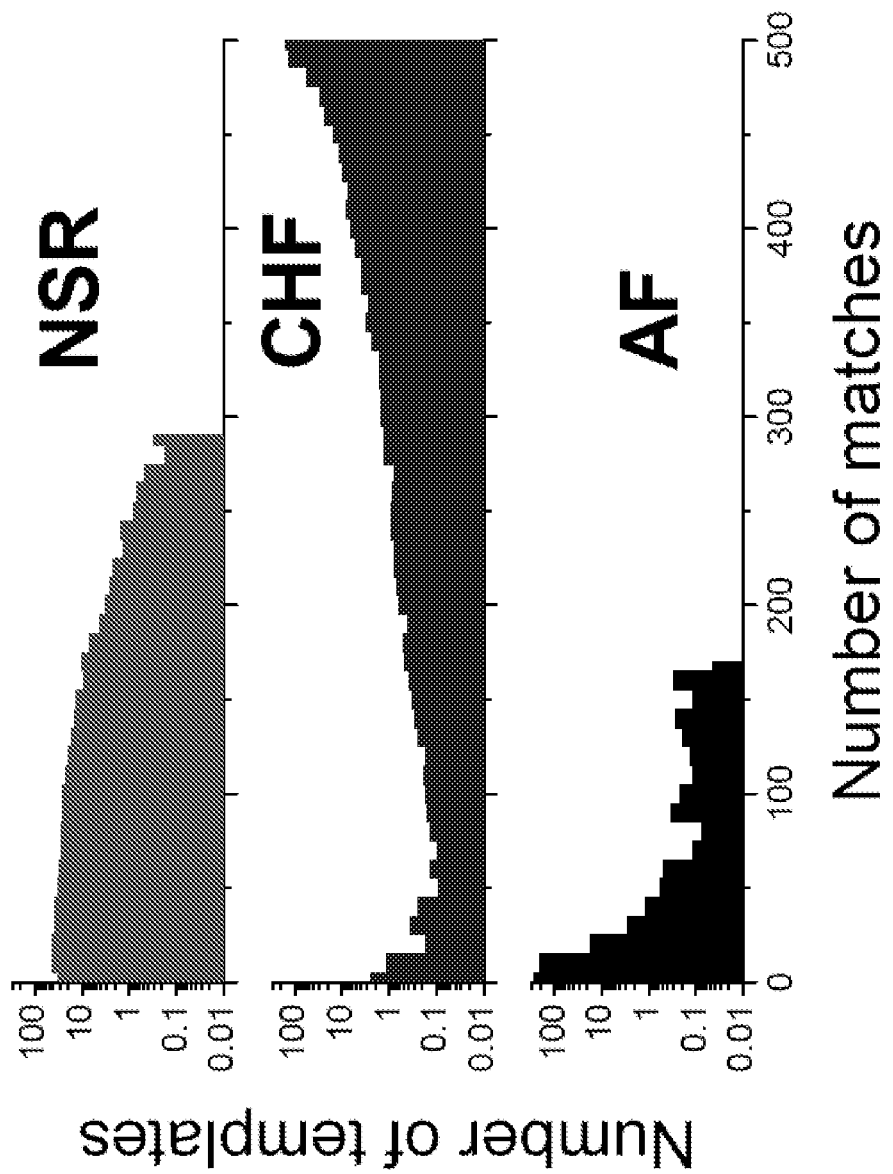
FIG. 4 illustrates histogram from an analysis of patients in the MIT-BIH database determining a number of matching intervals on average in 500 interval time series.

FIG. 4 shows histograms representing entropy measures for normal (top), CHF (middle) and AF (bottom) patients in the MIT-BIH databases. In each n-beat segment, the general method is to count the number of matches that were found for each interval. For m=1, for example, there are n intervals, and each can find as many as n−1 matches. To examine the results, we made histograms of the frequency of intervals having specified numbers of matches. Each 24-hour record was divided into 500 intervals, and the histograms were averaged. m=2 and r=20 msec. There are large phenotypic differences.

Figure 6:
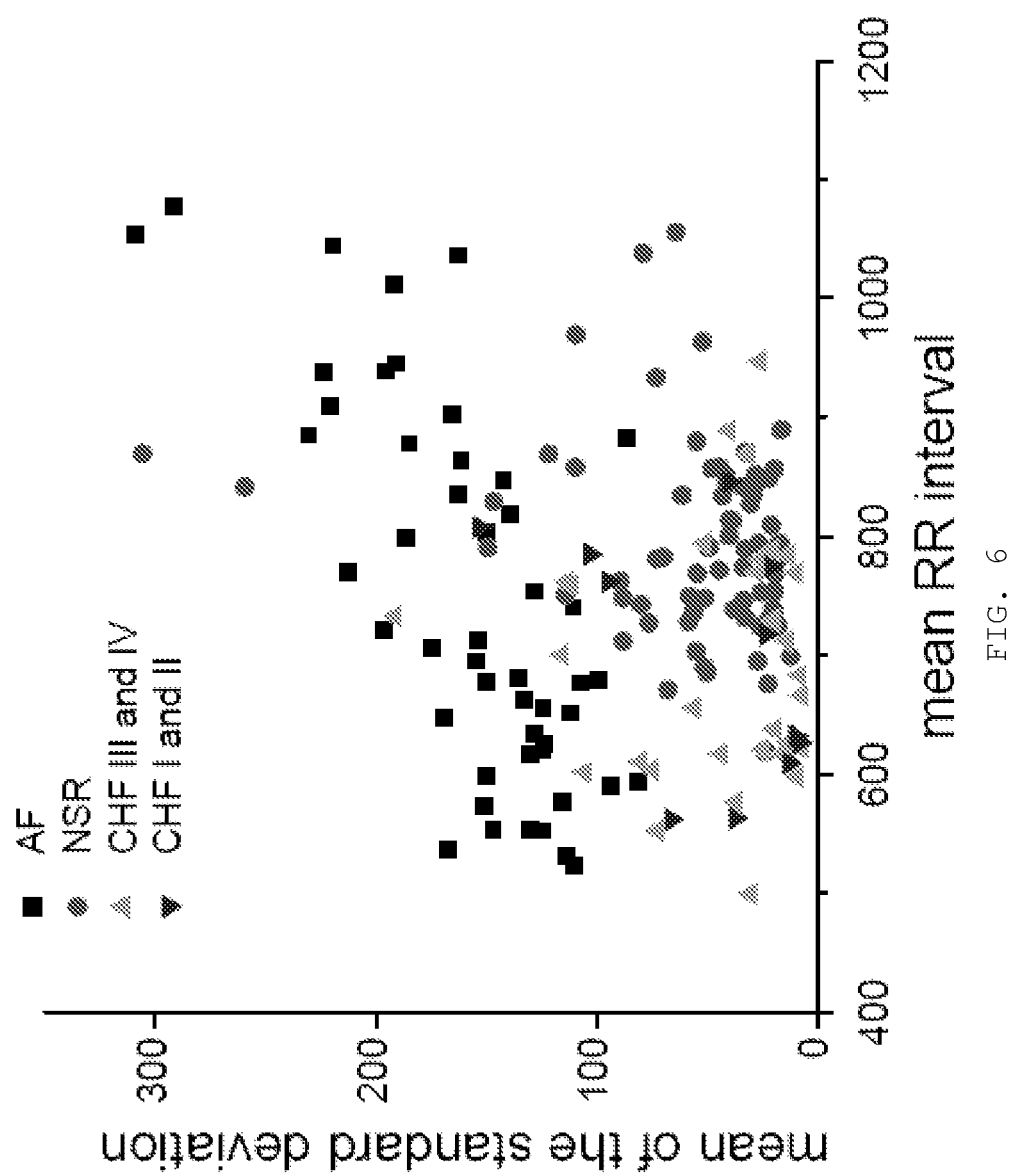
FIG. 6 is a scatter plot distinguishing between patients with AF, NSF and CHF.
Figure 7:
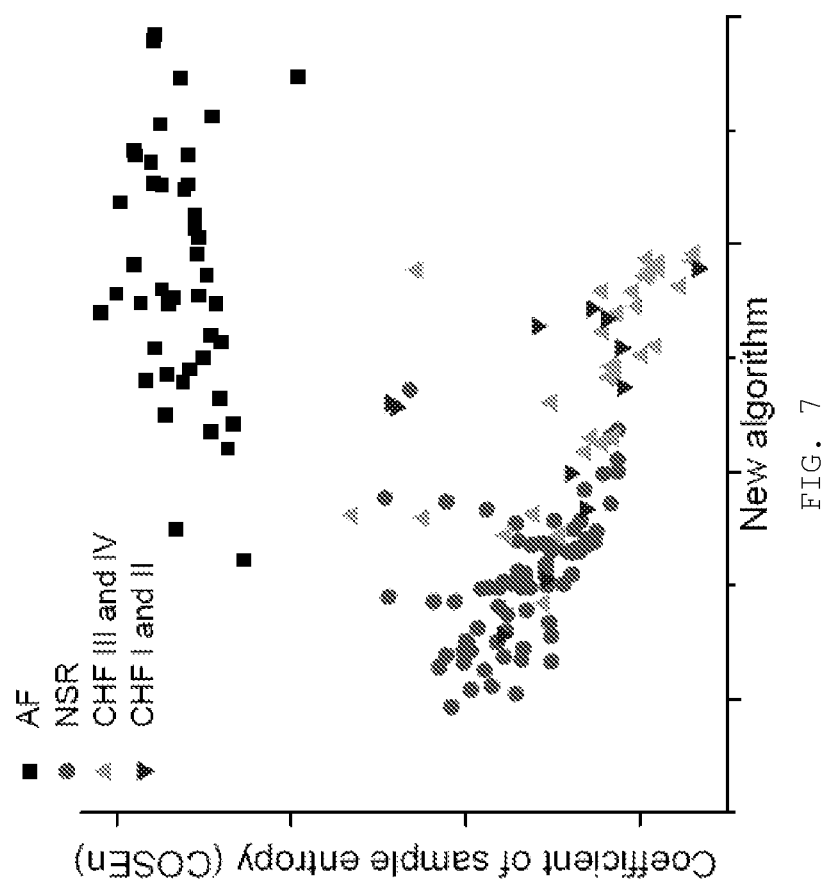
FIG. 7 illustrates results from a regression model using data from an embodiment of the present disclosure and COSEn in a scatter plot showing differentiation of patients with AF, NSF and CHF.

FIG. 7 illustrates how AF, NSR and CHF patients in the MIT-BIH database are distinguished using the two measures COSEn and the matching algorithm disclosed herein, which is based on the histograms on the left. These results are from an analysis of 12-beat samples every 30 minutes from 24-hour Holter monitor recordings, and improve greatly over existing measures such as heart rate and heart rate variability, results of which are shown in FIG. 6.

Thus, the disclosed matching algorithm should provide an accurate estimate of the degree of CHF burden in patients with single lead ICDs, and should be useful in early detection of deterioration and impending CHF hospitalization. In addition, it can be used to calculate an AF burden in conjunction with or separate from COSEn analysis. Both COSEn and the disclosed matching algorithm are computationally efficient (only a few extra steps are required to employ the disclosed matching algorithm), and together they offer new opportunities for informing clinicians about AF and CHF burdens in at-risk patients.

Entropy estimation is limited by the fact that it is fundamentally a ratio of 2 counts (expressed as the negative log), the numbers of matches of intervals of length m and m+1. While we have emphasized the importance of adequate numbers of counts of both types, we have not until now investigated the counts themselves. When given an entropy result of 0.693, we can tell that the ratio of the counts is 0.5, but we cannot tell whether the counts themselves were 5/10 or 50,000/100,000. It is conceivable that two time series with the same entropy result might have very different properties. This is especially possible in the case of RR interval time series where clinicians seek to detect CHF among patients with NSR. This is because patients with CHF can have much lower heart rate variability (HRV) than normals even though both groups have NSR. Indeed, many measures of HRV that can distinguish CHF from normals are based on aspects of reduced variability as measured in the time- and frequency-domains. Thus, low HRV should increase the number of matching intervals, and a strategy that employs a count of matching intervals as well as other measures of entropy should have increased diagnostic performance.

Figure 5:
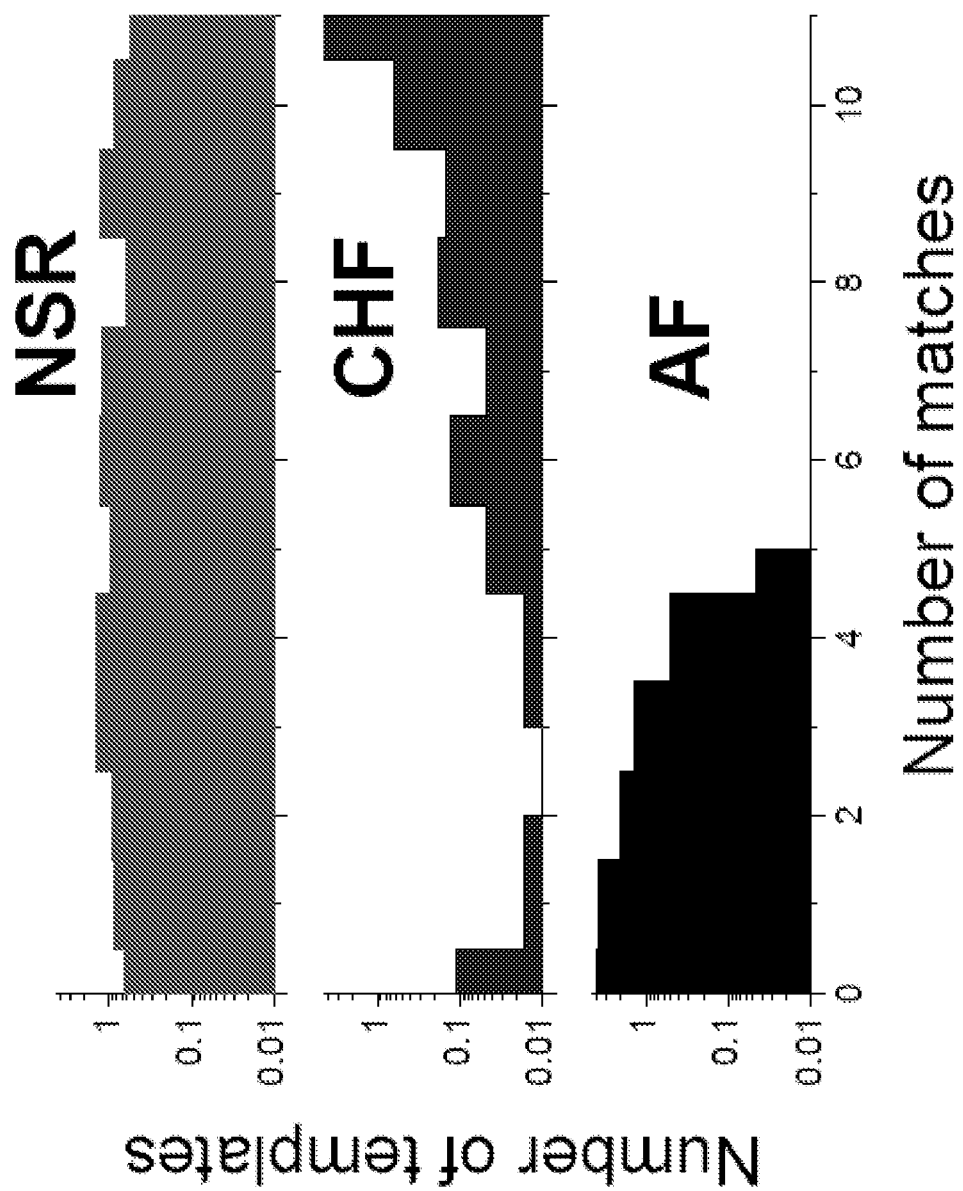
FIG. 5 depicts a histogram of average results from an analysis of patients from the MIT-BIH database, the histogram is very similar to that of FIG. 4, but only 12 instead of 500 interval time series were examined.

FIGS. 4 and 5 use the same records; however, FIG. 5 was analyzed much more sparsely—12 intervals at a time every 2400 beats, or about every 30 minutes (i.e., m=1 and r=20 msec). The differences between the histograms remain.

More specifically, FIGS. 4 and 5 show interval match count histograms for three groups of representative 24-Holter recordings from the MIT-BIH databases. From top to bottom of FIG. 4, the datasets were 500-beat segments from the NSR, CHF and AF databases. In each, the y-axis is the frequency of intervals of length m=2 that have the match count given on the x-axis. The left-most bin, for example, is the frequency of intervals in the 24 hour recording that each found 0 to 10 matches. The right-most bin is the frequency of intervals that matched 490 to 499 of the other intervals. The total of all the frequencies is the number of points in the 24-hour records, as each point is an interval.

The histograms look very different:

Histograms from NSR records are characterized by very few intervals that match the majority of points.

CHF records have relatively larger numbers of intervals in the left-most bins, representing intervals with a small numbers of matches. We ascribe these to premature ventricular or atrial beats. CHF records, on the other hand, have much larger numbers of intervals in the right-most bins. We ascribe these to intervals in a low variability baseline, where p(match) is high.

AF records are strikingly different. Most intervals have very few matches, as expected from the high variability of the RR interval time series and corresponding low p(match).

Thus, the observed interval match count histograms generally follow the theoretical results of FIG. 1, additional information important to discriminating CHF from NSR is available in the details of specific interval match count bins.

The large phenotypic differences between the histograms indicate that good distinction is possible. Since one of our goals is to implement the matching algorithms in implanted devices, where computing power is precious, we also examined these histograms for much shorter segments. The number of operations scales with $n^2$, so an effective diagnostic strategy using shorter segment lengths has appeal. In FIG. 5, we show results for 12-beat segments. In order to prepare for real-world implementation in implanted devices, where stored energy is at a premium, we only analyzed every $200^{th}$ segment, or every 2400 beats. This is about every 30 to 35 minutes, depending on the heart rate. For COSEn, we used m=1 and r=20 msec. (The justification for r=20 msec is that this led to the smallest proportion of intervals that were degenerate, that is, that found either no matches or matched every other interval.) Even at this sparse sampling, large phenotypic differences remain. It may be that even sparser sampling schemes have equally good results.

We used these phenotypic changes in interval match count histograms to develop a detection scheme based on multivariable regression. Table 3 shows diagnostic performance of detection algorithms based on conventional HR and HRV measures, and on the new measures COSEn and the interval match counts. Results are based on logistic regression models trained to distinguish the MIT-BIH NSR records from the MIT-BIH CHF records, and the ROC (receiver-operating characteristic) curve area is given. "Match counts" refers to the output of a regression model utilizing parameters extracted from the match count histogram. In this example, we used the average number of intervals having 0, 1, or 11 matches, and we used the average number of matches per interval. Other kinds of schemes also give good results. In particular, adding the mean RR interval to the match counts gave the highest diagnostic performance.

TABLE 3

Performance of multivariable predictive models

| predictor 1 | predictor 2 | ROC | p1 | p2 |
|---|---|---|---|---|
| S.D. | | 0.60 | * | |
| mean RR | | 0.78 | * | |
| S.D. | mean RR | 0.79 | | * |
| COSEn | | 0.78 | * | |
| match counts model | | 0.92 | * | |
| COSEn | match counts model | 0.89 | | * |
| average counts model | match counts model | 0.91 | * | * |
| match counts model | mean RR | 0.93 | * | * |

Predictors 1 and 2 are predictor variables in the multivariable regression models; ROC is receiver-operating characteristic curve area; p1 and 2 are the p-values on the coefficients of predictors 1 and 2, respectively, in the regression models, and * denotes p<0.05 for addition of independent information.

It is important to note that COSEn, which we developed to distinguish AF from NSR, does not add information to the new measures in detecting CHF. We implemented these predictive models in the MIT-BIH databases, and represented each Holter monitor record as a single measure based on analysis of 12 beats every 2400 beats. For the MIT-BIH AF records, we found that several had paroxysmal AF and fewer than 40 measures were available from the record. Accordingly, we added 20 24-hour Holter monitors from the University of Virginia (UVA) Heart Station that showed only AF.

FIGS. 6 and 7 show scatter plots of old and new measures. AF records are shown in black squares and combine records from the MIT-BIH AF database and from our own UVA Holter database. The other symbols are all from the MIT-BIH databases—NSR (red dots) and the CHF databases, containing 32 patients with severe CHF (classes III and IV, right-side up green triangles) and 12 patients with somewhat less severe CHF (classes I and II, upside down blue triangles).

FIG. 6 illustrates a scatter plot of conventional HRV measures for 12-beat segments sampled every 2400 beats for records in MIT-BIH AF, NSR and CHF databases, and 20 AF records from UVA. The scatter plot includes the results of standard measures of heart rate (x-axis, mean RR interval) and heart rate variability (mean of the standard deviation). Though HRV has been known for years to distinguish among these clinical conditions, we find little useful information in these settings.

FIG. 7 shows improved distinction using COSEn (y-axis) and a new measure, the average of a predictive model based on interval match count histograms.

As we have previously disclosed, COSEn separates AF well from the other records, which all are NSR but with varying degrees of CHF by clinical criteria. COSEn is not as effective, however, in detecting CHF.

In FIG. 7, there is good distinction among the NSR and CHF groups, consistent with the idea that the matching algorithm sorts records into a hierarchy along a gradient from no CHF to severe symptoms. AF is also distinguished on the y-axis due to the incorporation of COSEn data into the regression model.

Figure 8:
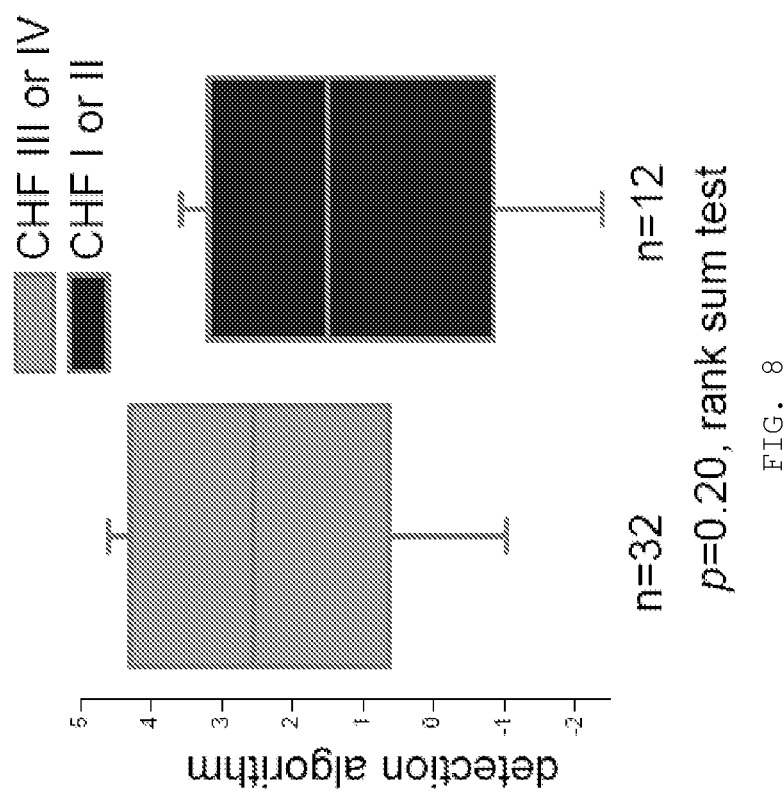
FIG. 8 illustrates a box plot showing a trend for higher diagnostic values in more severe class III and IV CHF patients.

To further test the idea that the new measure changed smoothly over a range of CHF severity, we compared records of patients from the MIT-BIH database with NYHA class I/II or class III/IV CHF. The box plot of FIG. 8 shows that there was a trend for higher values for the new algorithm in the more severe class III and IV CHF patients.

New entropy-based measures of RR interval time series give information on the presence and degree of CHF. Remarkably good diagnostic performance is available from only sparsely sampled data sets—12 beats every 30 minutes. This new set of measures should be useful in implanted devices with even a single ventricular lead to help monitor CHF in patients at risk.

Turning to FIG. 1, it is contemplated that embodiments of the invention may be practiced using a computer system. FIG. 1 is an illustrative block diagram for a computer system 100 for implementation of an exemplary embodiment or portion of an embodiment of present invention. For example, a method or system of an embodiment of the present invention may be implemented using hardware, software or a combination thereof and may be implemented in one or more computer systems or other processing systems, such as personal digit assistants (PDAs). In an example embodiment, the invention was implemented in software running on a general purpose computer 100 as illustrated in FIG. 1. The computer system 100 may includes one or more processors, such as processor 104. The Processor 104 is connected to a communication infrastructure 106 (e.g., a communications bus, cross-over bar, or network). The computer system 100 may include a display interface 102 that forwards graphics, text, and other data from the communication infrastructure 106 (or from a frame buffer not shown) for display on the display unit 830.

The computer system 10 may also include a main memory 108, preferably random access memory (RAM), and may include a secondary memory 110. The secondary memory 110 may include, for example, a hard disk drive 112 and/or a removable storage drive 114, representing a floppy disk drive, a magnetic tape drive, an optical disk drive, a flash memory, etc. The removable storage drive 114 reads from and/or writes to a removable storage unit 118 in a well known manner. Removable storage unit 118, represents a floppy disk, magnetic tape, optical disk, etc. which is read by and written to by removable storage drive 114. As will be appreciated, the removable storage unit 118 includes a computer usable storage medium having stored therein computer software and/or data.

In alternative embodiments, secondary memory 110 may include other means for allowing computer programs or other instructions to be loaded into computer system 100. Such means may include, for example, a removable storage unit 122 and an interface 120. Examples of such removable storage units/interfaces include a program cartridge and cartridge interface (such as that found in video game devices), a removable memory chip (such as a ROM, PROM, EPROM or EEPROM) and associated socket, and other removable storage units 122 and interfaces 120 which allow software and data to be transferred from the removable storage unit 122 to computer system 100.

The computer system 100 may also include a communications interface 124. Communications interface 124 allows software and data to be transferred between computer system 100 and external devices. Examples of communications interface 824 may include a modem, a network interface (such as an Ethernet card), a communications port (e.g., serial or parallel, etc.), a PCMCIA slot and card, a modem, etc. Software and data transferred via communications interface 124 are in the form of signals 828 which may be electronic, electromagnetic, optical or other signals capable of being received by communications interface 124. Signals 128 are provided to communications interface 124 via a communications path (i.e., channel) 126. Channel 126 (or any other communication means or channel disclosed herein) carries signals 128 and may be implemented using wire or cable, fiber optics, blue tooth, a phone line, a cellular phone link, an RF link, an infrared link, wireless link or connection and other communications channels.

In this document, the terms "computer program medium" and "computer usable medium" are used to generally refer to media or medium such as removable storage drive 114, a hard disk installed in hard disk drive 112, and signals 128. These computer program products are means for providing software to computer system 100. The computer program product may comprise a computer useable medium having computer program logic thereon. The invention includes such computer program products. The "computer program product" and "computer useable medium" may be any computer readable medium having computer logic thereon.

Computer programs (also called computer control logic or computer program logic) may be stored in main memory 108 and/or secondary memory 110. Computer programs may also be received via communications interface 124. Such computer programs, when executed, enable computer system 100 to perform the features of the present invention as discussed herein. In particular, the computer programs, when executed, enable processor 104 to perform the functions of the present invention. Accordingly, such computer programs represent controllers of computer system 100.

In an embodiment where the invention is implemented using software, the software may be stored in a computer program product and loaded into computer system 100 using removable storage drive 114, hard drive 112 or communications interface 124. The control logic (software), when executed by the processor 104, causes the processor 104 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in SPSS control language or C++ programming language, but could be implemented in other various programs or other programs known to those skilled in the art.

Embodiments of the present disclosure may extend the entropy estimation to two or more simultaneous time series of parameters measured by the device. The present disclosure relates cross-entropy measures optimized for simultaneous time series for data using a different scale and of a different character. These cross-entropy approaches may be extended to multiple simultaneous time series recorded by implantable devices, and require optimizations because of the differences in sampling rates, scales, and dynamics inherent in the recordings of HR, HR parameters (especially the entropy measures developed elsewhere in this specification), patient activity, body temperature, AF and other arrhythmia burden, trans-thoracic impedance, and intra-cardiac pressures.

Thus, a part of some embodiments is to not only include entropy rate estimates of RR intervals and other physiologic signals, but to incorporate global measures of entropy rate for the entire collection of series. We developed multidimensional entropy estimates for this task.

For the case of two signals, measures of entropy rate have already been developed that extend SampEn to Cross-SampEn. This method requires that the two signals have similar scale and location, which can be achieved by first standardizing each signal by subtracting the mean and dividing by the standard deviation. This step then allows candidate match intervals from the first signal to be sought in the second signal. By accumulating the total number of cross-matches of various interval lengths m, conditional probabilities and densities can be calculated and natural logarithms taken in the same manner as SampEn and differential or quadratic entropy rate. One approach to analyzing more than two signals for detecting CHF is to calculate all pair-wise combinations of the cross-entropy rate.

Some embodiments include several enhancements to estimating entropy rate for p signals, where p>1. First, the idea of an interval vector of length m can be extended to a interval matrix of size m times p. In this case, each column represents the corresponding standardized signal value at a particular time. In an analogous way to SampEn, interval matrix matches will require that all elements be within a specified tolerance r. Proceeding in this way leads to a global measure of entropy rate.

A second approach is to use ways of determining matches using distance measures other than a simple tolerance requirement component by component, for example Euclidean distance (the square root of the sum of the component distances squared). This approach recognizes that simply standardizing the signals has limitations and does not incorporate the correlations among the signals. An improved distance measure (used previously in nearest-neighbor analysis) between the p signals at two particular times can be achieved using the Mahalanobis distance which specifically accounts for the correlation. This distance first multiplies the signal vector by a matrix that makes the components uncorrelated and then taking the Euclidean distance.

In implanted cardiac devices and in many other kinds of monitors, signals are sampled at different rates. For the multidimensional entropy measures reported here, the signal information is summarized at specified time increments (hourly, for example) for inclusion on the mathematical calculations described. The summarization may be a robust marker of the central value such as the median, or detect abnormalities of interest. Since, for example, reduced HRV is associated with illness but may visit many levels of variability in the course of an hour, a suitable summary measure is the $10^{th}$ percentile lowest value observed. Thus, the summarization strategies play key roles in the multidimensional detection schemes.

Some of the measures may vary by time of day, so clock time is another important dimension to include in the final predictive schemes. Patients known to have episodes of arrhythmia such as atrial fibrillation may generate misleading monitoring results if AF is not detected and quantified, as naïve measures of HRV will return spuriously normal results. Thus, families of predictive algorithms tailored for past findings are required.

Those of ordinary skill may vary the methods and apparatus for detecting an abnormal cardiac rhythm and patient clinical status without varying from the scope of the invention as defined in the appended claims.

What is claimed is:

1. A method of detecting abnormal cardiac rhythms and clinical status of a subject comprising:
   obtaining physiological data obtained from a sampling device from the subject comprising one or more series of intervals;
   calculating entropy related data using a computer processing device configured for processing the physiological data based on the one or more series of intervals, wherein the entropy related data are new entropy based measures of time series comprising:
   interval match count histograms, and
   histogram derived measures in which the y-axis of the histograms is the frequency of intervals of length m that have the match count given on the x-axis; and
   generating a diagnostic output based on the entropy related data.

2. The method of claim 1, wherein generating the diagnostic output comprises using a regression model to combine the numbers of matching intervals.

3. The method of claim 1, wherein the physiological data comprises two or more series of intervals obtained simultaneously from different physiological signals.

4. The method of claim 1 further comprising separating the one or more series of intervals into a plurality of subsets of the one or more series of intervals.

5. The method of claim 4, wherein calculating the entropy related data further comprises averaging entropy related data from each of the plurality of the subsets of the one or more series of intervals.

6. The method of claim 4, wherein the subsets of the one or more series of intervals comprise less than 13 intervals.

7. The method of claim 1, wherein generating the diagnostic output further comprises using coefficient of sample entropy (COSEn).

8. The method of claim 1 further comprising producing an output to a medical care provider to diagnose abnormal cardiac rhythms and clinical status of the subject.

9. The method of claim 1, wherein the one or series of intervals comprises a number of samples during one period of a cardiac rhythm.

10. The method of claim 1, wherein calculating entropy related data based on the interval match count histograms further comprises a tolerance value (r) for determining whether two or more intervals match.

11. The method of claim 9, wherein the data from the cardiac rhythm of a subject comprises samples from an EKG waveform.

12. The method of claim 1, further comprising calculating an absolute entropy measurement.

13. The method of claim 12, wherein the absolute entropy measurement is a coefficient of sample entropy (COSEn).

14. An apparatus for detecting abnormal cardiac rhythms and clinical status of a subject comprising:
    a sampling device for obtaining physiological data from the subject comprising a one or more series of intervals;
    a computer processing device configured for processing the physiological data from the subject into entropy related data and producing a diagnostic result, wherein the entropy related data are new entropy based measures of time series comprising:
    interval match count histograms, and
    histogram derived measures in which the y-axis of the histograms is the frequency of intervals of length m that have the match count given on the x-axis; and
    an result device for rendering the diagnostic output.

15. The apparatus of claim 14, wherein the sampling device comprises an EKG machine.

16. The apparatus of claim 14, wherein producing the diagnostic result comprises running a regression model on the entropy related data.

17. The apparatus according to claim 14, wherein the physiological data is representative of a cardiac rhythm and clinical status of the subject.

* * * * *